US011304660B2

(12) United States Patent
Paquet et al.

(10) Patent No.: US 11,304,660 B2
(45) Date of Patent: Apr. 19, 2022

(54) ADHESIVE EXTENDER FOR MEDICAL ELECTRODE AND USE THEREOF WITH WEARABLE MONITOR

(71) Applicant: ICENTIA INC., Québec (CA)

(72) Inventors: Pierre Paquet, Quebec (CA); David Levesque, St-Augustin-de-Desmaures (CA); Pierre Fecteau, St-Augustin-de-Desmaures (CA)

(73) Assignee: ICENTIA INC., Quebec (CA)

( * ) Notice: Subject to any disclaimer, the term of this patent is extended or adjusted under 35 U.S.C. 154(b) by 137 days.

(21) Appl. No.: 16/093,151

(22) PCT Filed: Apr. 12, 2016

(86) PCT No.: PCT/CA2016/050422
§ 371 (c)(1),
(2) Date: Oct. 12, 2018

(87) PCT Pub. No.: WO2017/177299
PCT Pub. Date: Oct. 19, 2017

(65) Prior Publication Data
US 2019/0183426 A1    Jun. 20, 2019

(51) Int. Cl.
*A61B 5/06* (2006.01)
*A61B 5/00* (2006.01)
(Continued)

(52) U.S. Cl.
CPC .......... *A61B 5/7207* (2013.01); *A61B 5/0006* (2013.01); *A61B 5/274* (2021.01);
(Continued)

(58) Field of Classification Search
CPC . A61B 5/7207; A61B 5/68335; A61B 5/0006; A61B 5/04085; A61B 5/0416;
(Continued)

(56) References Cited

U.S. PATENT DOCUMENTS 2,425,945 A    8/1947  Leach
D232,590 S    8/1974  Moore
(Continued)

FOREIGN PATENT DOCUMENTS

EP    2172164 A1    4/2010
JP    H04296893 A    10/1992
(Continued)

OTHER PUBLICATIONS

Rochester EverLast Disc (Cup) Electrodes with Silicone wire, from the Internet, http://ep.yimg.com/ay/yhst-129045937317690/bio-potential-gold-6-ft-5-pk-9.jpg.
(Continued)

*Primary Examiner* — Ankit D Tejani
*Assistant Examiner* — Joshua Brendon Solomon
(74) *Attorney, Agent, or Firm* — Alexandre Daoust; Norton Rose Fulbright Canada LLP

(57) ABSTRACT

The adhesive extenders can be used to cover and surround the medical electrode assemblies on the skin of a patient. A wearable monitor can be used to obtain electrogram data from the patient via the electrodes.

28 Claims, 12 Drawing Sheets

(51) Int. Cl.
*A61B 5/274* (2021.01)
*A61B 5/282* (2021.01)
*A61B 5/333* (2021.01)
*A61B 5/25* (2021.01)

(52) U.S. Cl.
CPC .............. *A61B 5/282* (2021.01); *A61B 5/333* (2021.01); *A61B 5/6833* (2013.01); *A61B 5/68335* (2017.08); *A61B 5/25* (2021.01); *A61B 2560/045* (2013.01); *A61B 2562/16* (2013.01)

(58) Field of Classification Search
CPC ... A61B 5/0432; A61B 5/6833; A61B 5/0408; A61B 2560/045; A61B 2562/16
See application file for complete search history.

(56) References Cited

U.S. PATENT DOCUMENTS

| | | | |
|---|---|---|---|
| 4,094,309 A | 6/1978 | Grzenia | |
| 4,114,263 A | 9/1978 | Szpur | |
| 4,207,904 A | 6/1980 | Greene | |
| D277,938 S | 3/1985 | Knute | |
| 4,580,339 A * | 4/1986 | Ioffe | A61N 1/0456 29/825 |
| 4,633,879 A | 1/1987 | Ong | |
| D326,716 S | 6/1992 | Mortara | |
| 5,184,620 A | 2/1993 | Cudahy et al. | |
| 5,292,312 A | 3/1994 | Delk et al. | |
| 5,391,250 A | 2/1995 | Cheney, II et al. | |
| 5,511,548 A | 4/1996 | Riazzi et al. | |
| 5,846,217 A | 12/1998 | Beck et al. | |
| 5,980,456 A | 11/1999 | Falcone | |
| D424,699 S | 5/2000 | Allen | |
| 6,120,792 A | 9/2000 | Juni | |
| 6,128,521 A | 10/2000 | Marro et al. | |
| D433,755 S | 11/2000 | Mastrototaro et al. | |
| 6,409,659 B1 | 6/2002 | Warner et al. | |
| 6,967,652 B1 | 11/2005 | Nubling et al. | |
| 8,428,682 B1 | 4/2013 | Rood et al. | |
| 8,613,708 B2 | 12/2013 | Bishay et al. | |
| 8,989,850 B2 | 3/2015 | Balda | |
| 2005/0154325 A1* | 7/2005 | Lauter | A61B 5/0452 600/515 |
| 2005/0222510 A1 | 10/2005 | Hadley et al. | |
| 2005/0222511 A1 | 10/2005 | Hadley et al. | |
| 2005/0222512 A1 | 10/2005 | Hadley et al. | |
| 2005/0222513 A1 | 10/2005 | Hadley et al. | |
| 2005/0234362 A1 | 10/2005 | Kaiser et al. | |
| 2005/0245839 A1 | 11/2005 | Stivoric et al. | |
| 2008/0097231 A1 | 4/2008 | Baida et al. | |
| 2010/0075527 A1* | 3/2010 | McIntire | H01R 4/48 439/357 |
| 2011/0021936 A1 | 1/2011 | Luo | |
| 2011/0160601 A1 | 6/2011 | Wang et al. | |
| 2014/0100432 A1 | 4/2014 | Golda et al. | |
| 2016/0007877 A1* | 1/2016 | Felix | A61B 5/04087 600/523 |
| 2016/0228060 A1* | 8/2016 | Mazar | A61B 5/6833 |
| 2017/0172413 A1* | 6/2017 | Chakravarthy | A61B 5/0472 |
| 2017/0319095 A1 | 11/2017 | Felix et al. | |

FOREIGN PATENT DOCUMENTS

| | | |
|---|---|---|
| JP | 2002045345 A | 2/2002 |
| WO | 2007103835 A2 | 9/2007 |
| WO | 2013065147 A1 | 5/2013 |
| WO | 2017177299 A1 | 10/2017 |

OTHER PUBLICATIONS

Tyagi et al., QRS Detection using EMD and First Order Gaussian Differentiator, International Journal of Engineering Research & Technology (IJERT), ISSN: 2278-0181, vol. 3 Issue 2, Feb. 2014.
ZIO XT Patch for diagnosis of cardiac arrhytmia, Health Policy Advisory Committee on Technology, Technology Brief; Mar. 2015.
Zhang et al., "A Wireless ECG Plaster for Real-Time Cardiac Health Monitoring in Body Sensor Networks", Biomedical Circuits and Systems Conference (BIOCAS), 2011 IEEE, Nov. 10, 2011 (Nov. 10, 2011), pp. 205-208, XP032076560, DOI: 10.1109/BIOCAS.2011.6107763, ISBN: 978-1-4577-1469-6.

* cited by examiner

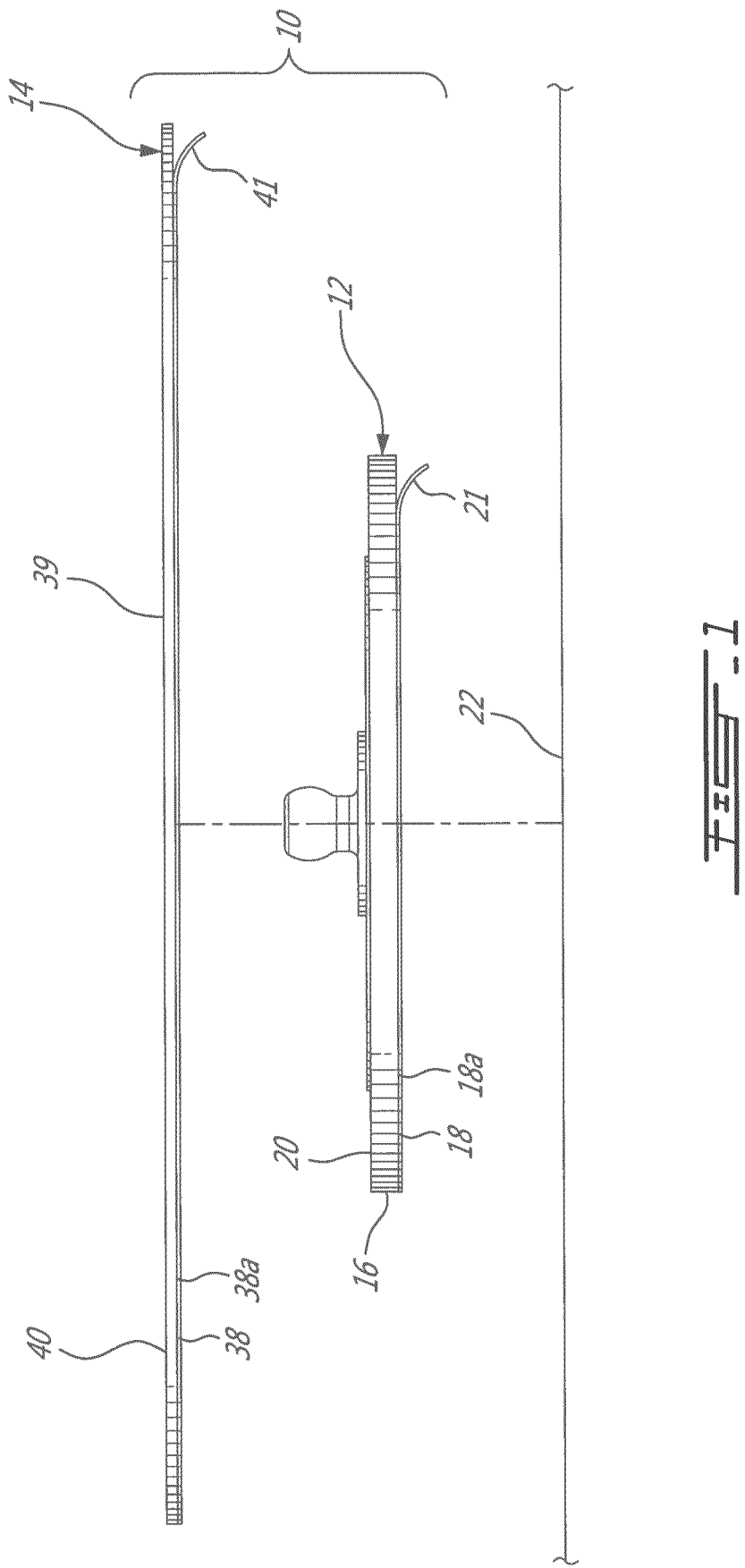

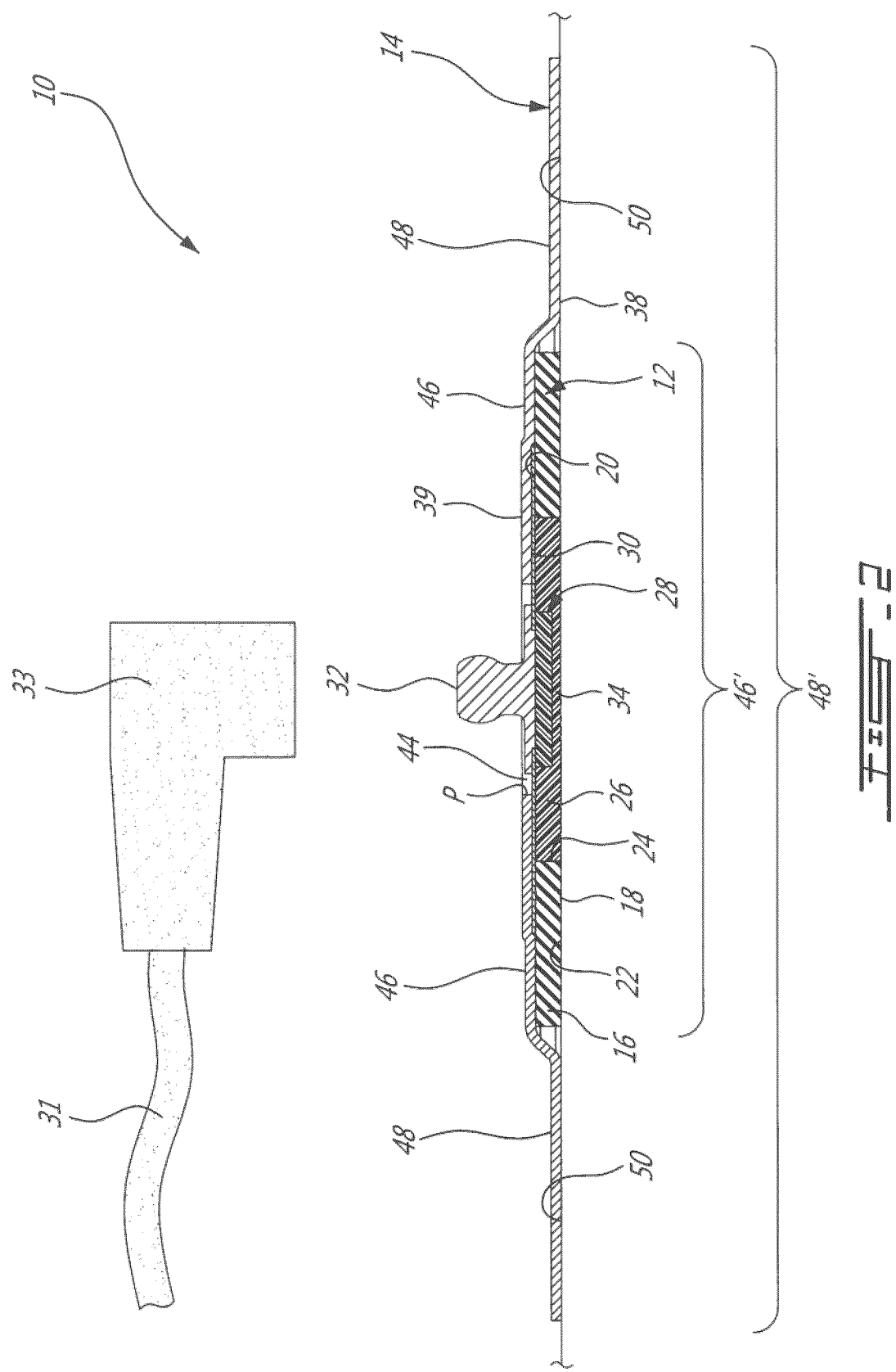

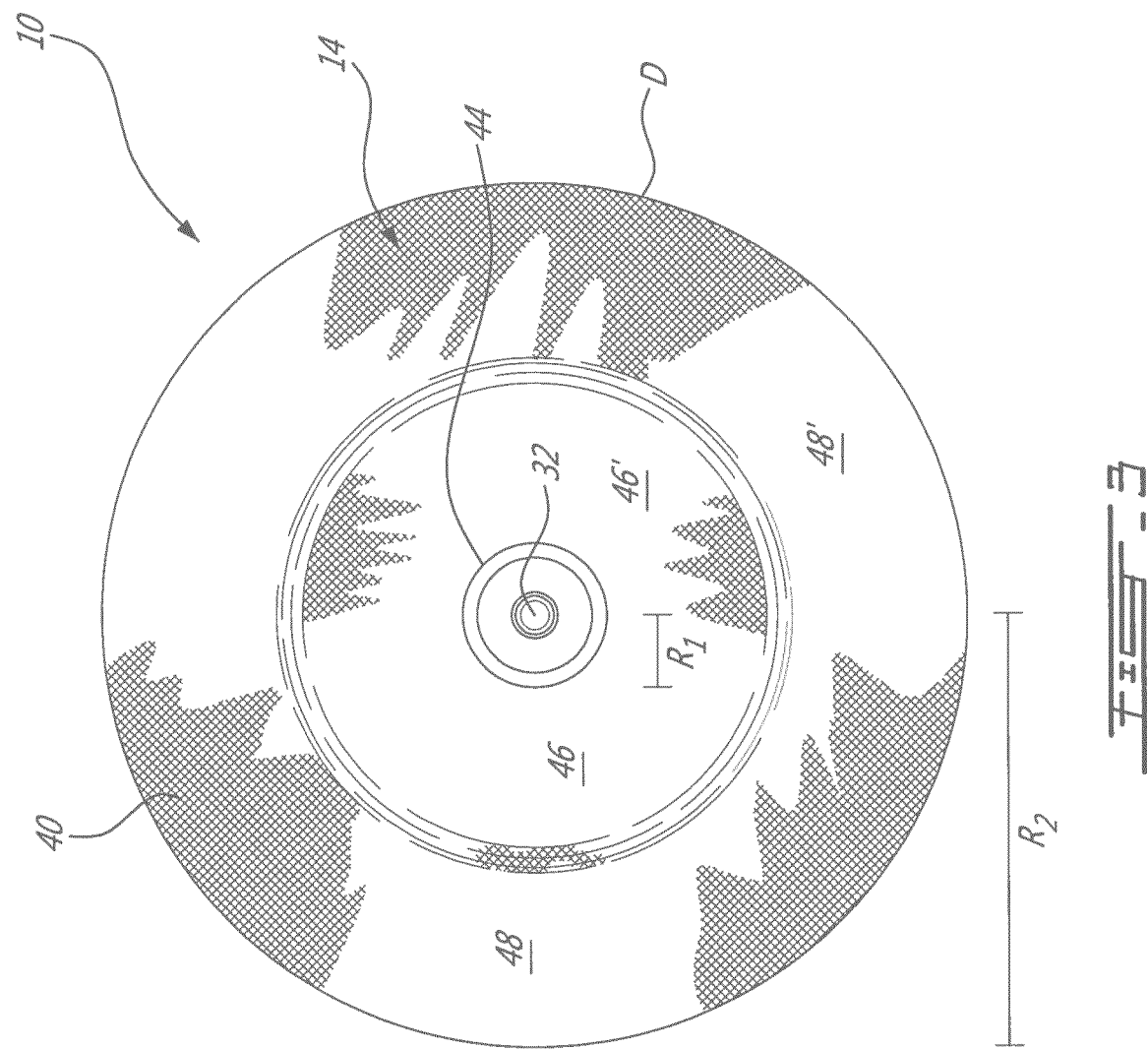

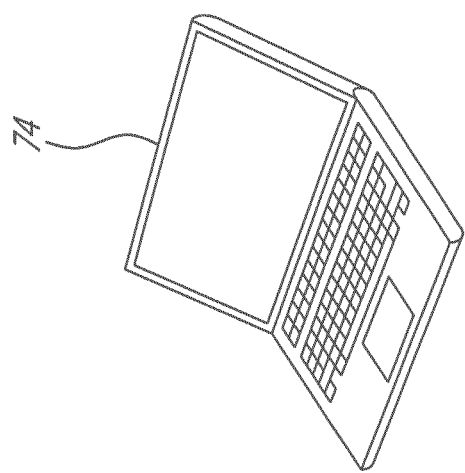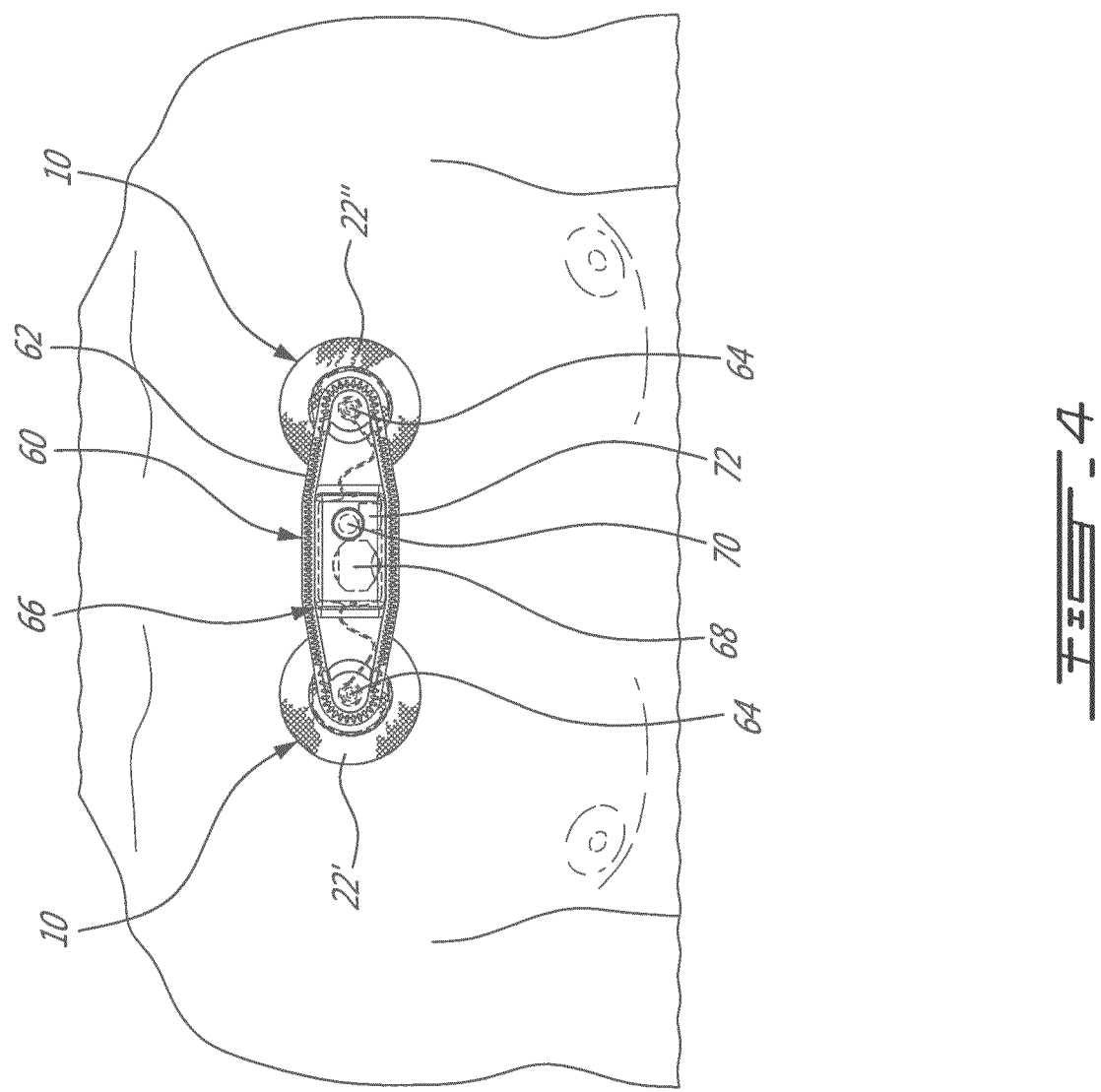

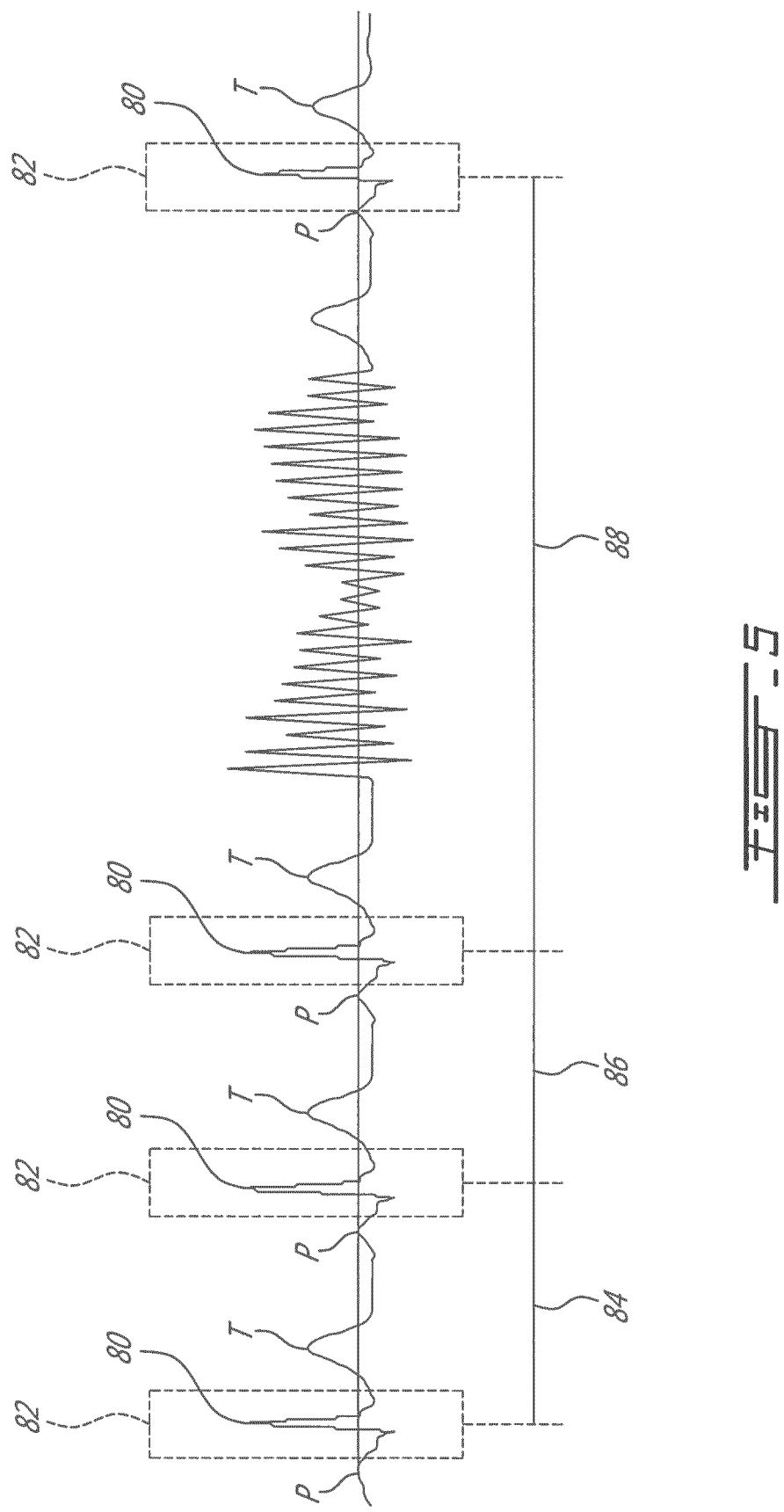

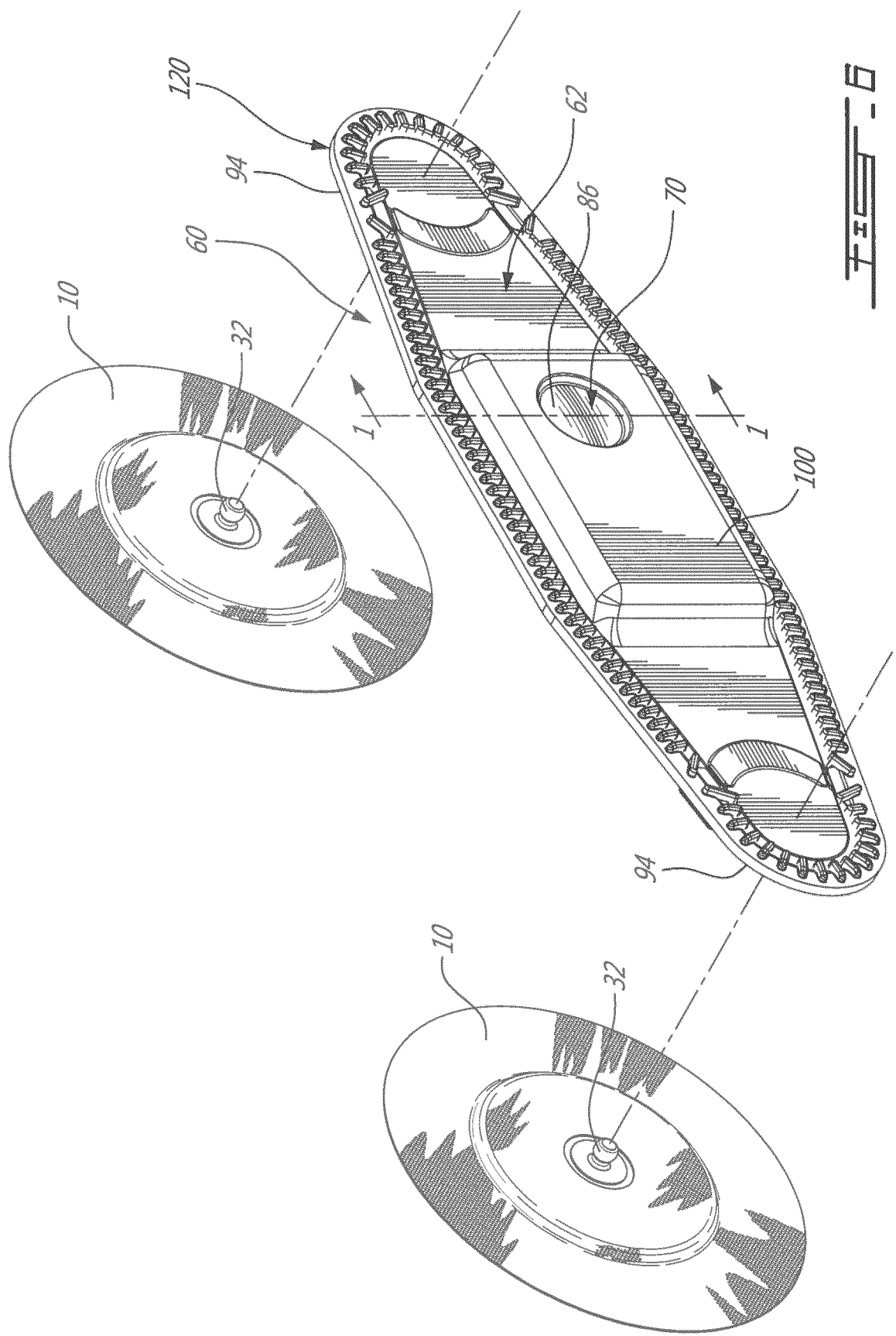

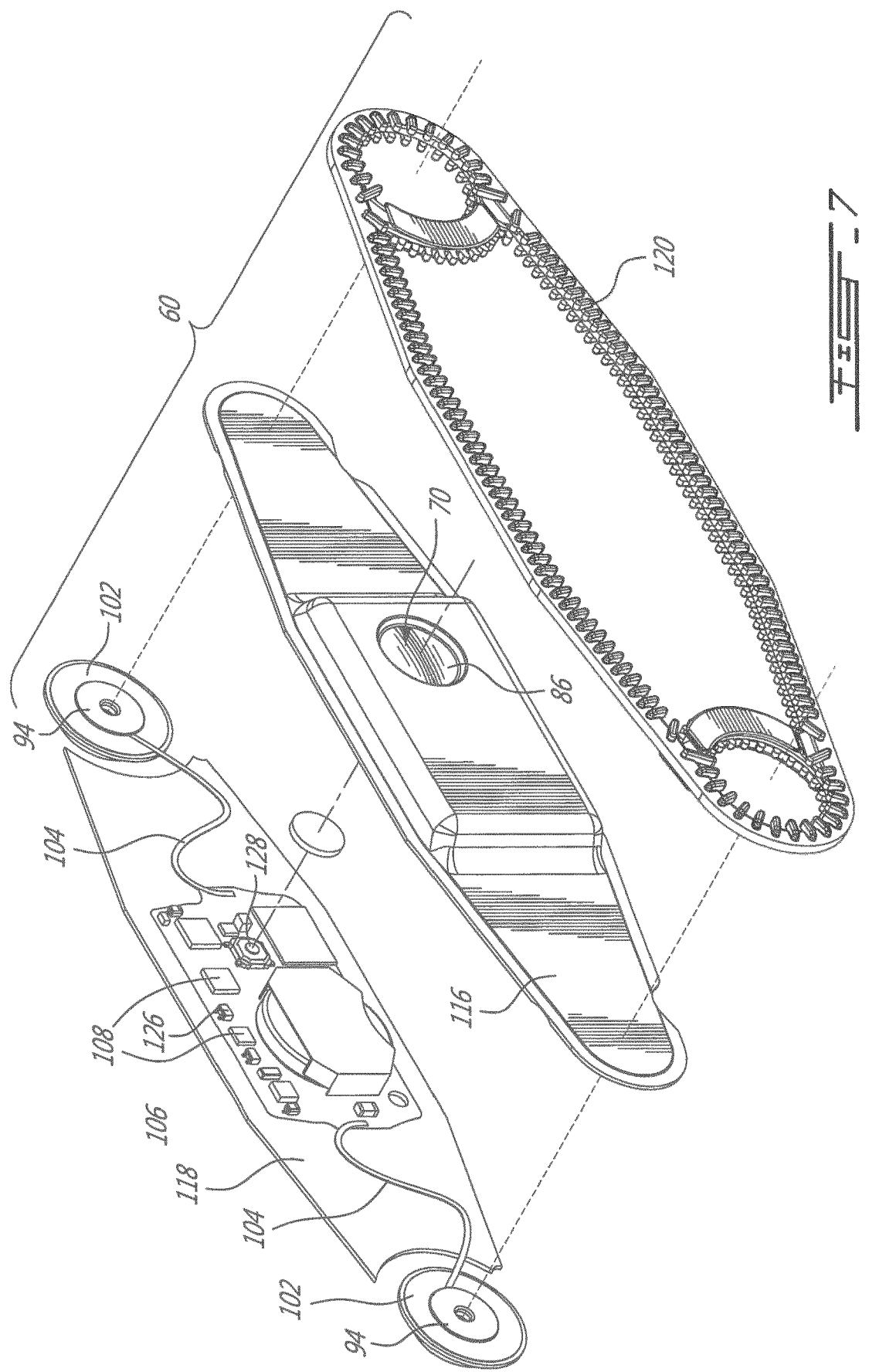

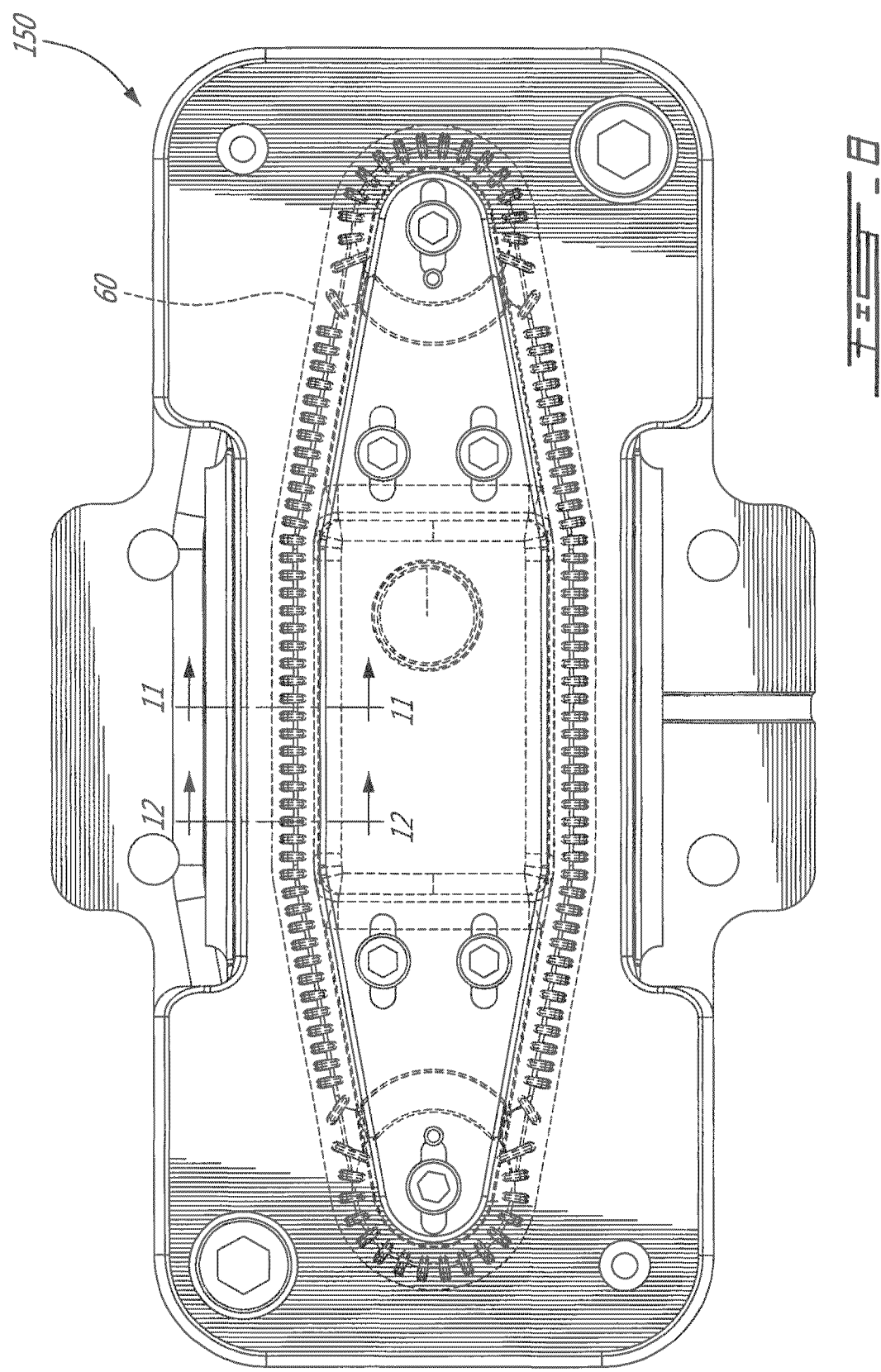

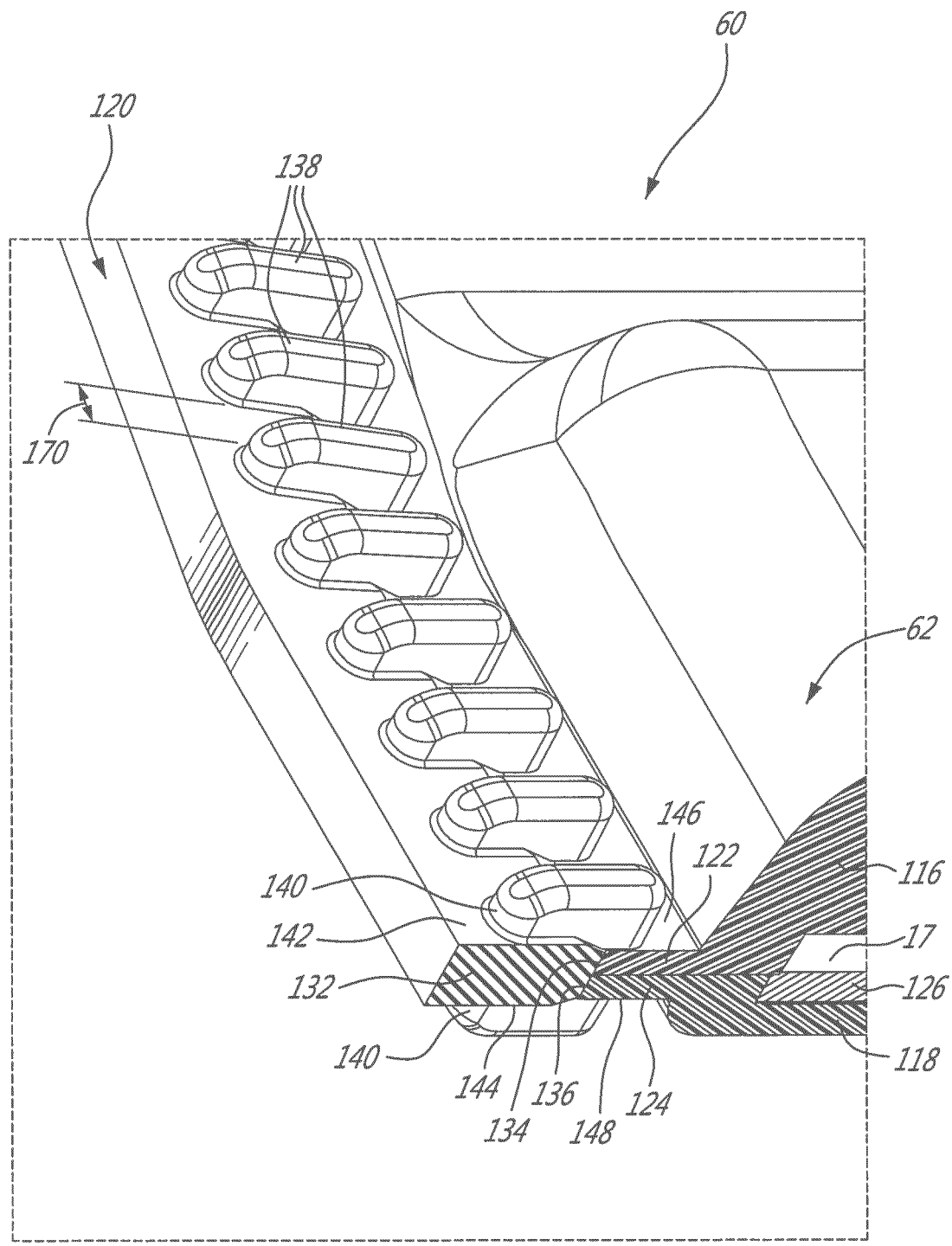

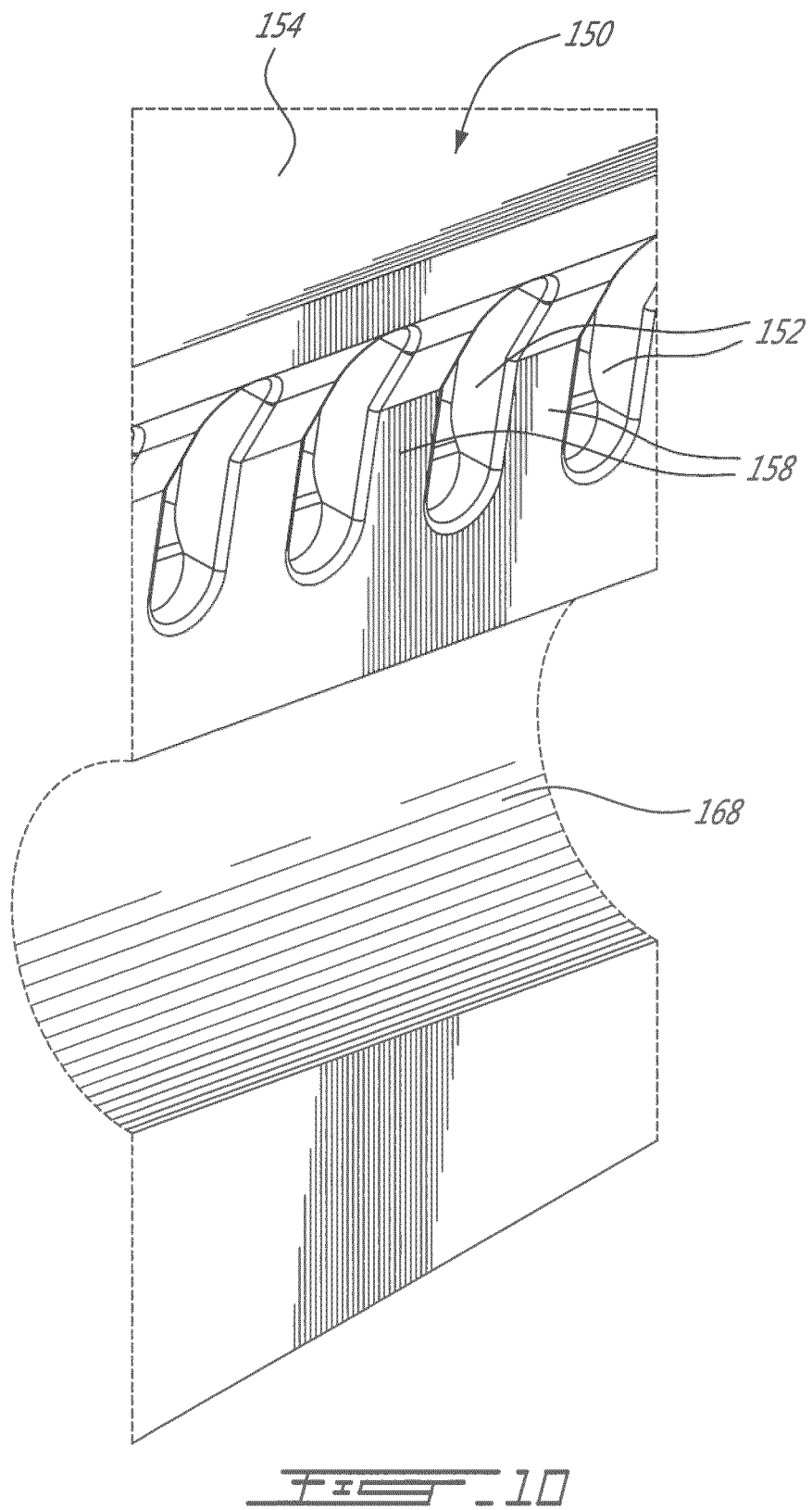

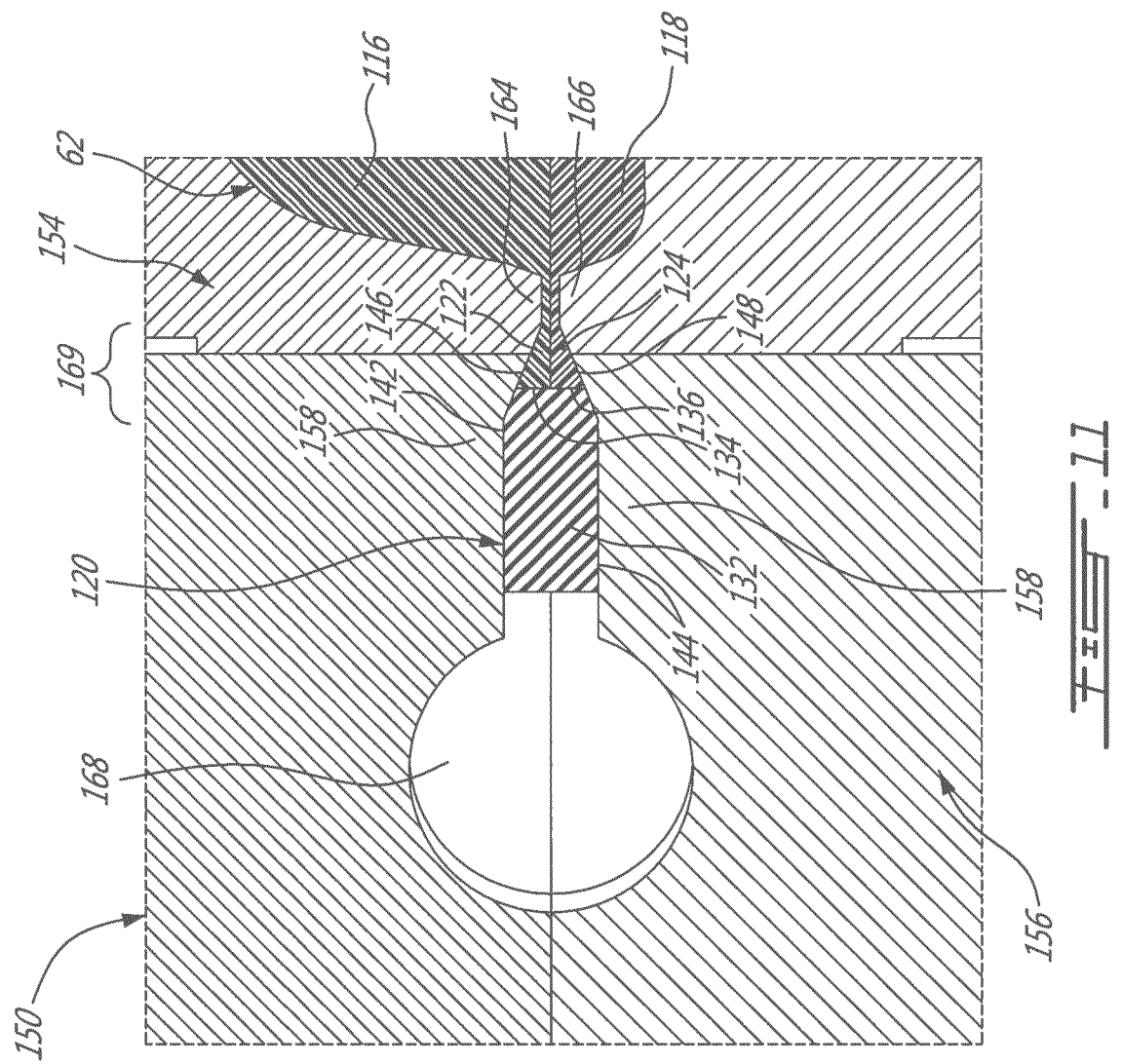

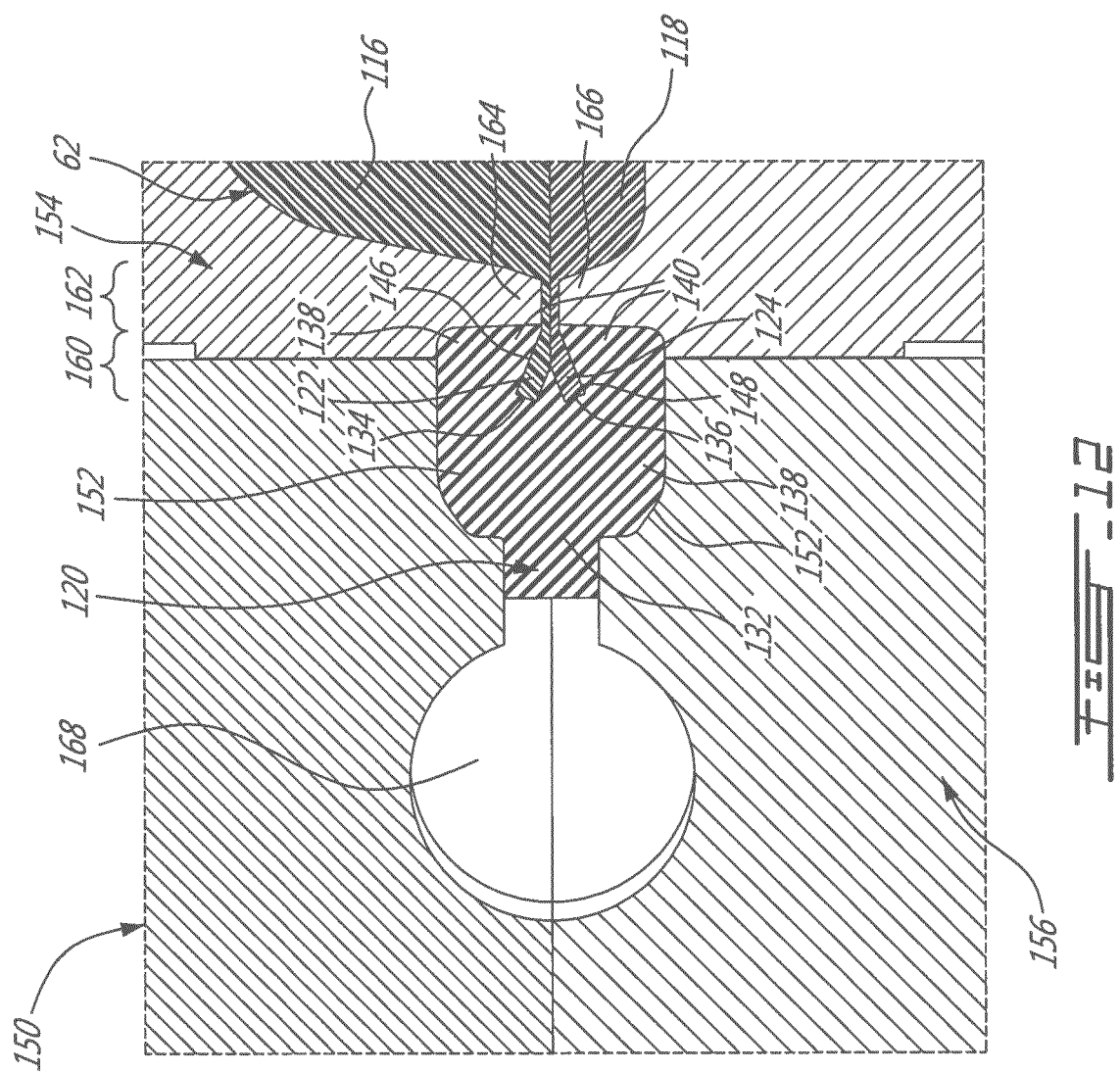

ADHESIVE EXTENDER FOR MEDICAL ELECTRODE AND USE THEREOF WITH WEARABLE MONITOR

FIELD

The improvements generally relate to the field of devices and methods for obtaining electrogram data from a patient via medical electrode assemblies.

BACKGROUND

A medical electrode assembly can be used for monitoring an electrical signal from the body of a patient using a monitor. Medical electrode assemblies are widely used for obtaining electrogram data such as electrocardiogram (ECG) data representing the electrical activity of the heart and an electroencephalogram (EEG) representing the electrical activity of the brain.

Medical electrode assemblies are usually self-adhesive and include connectors that allow them to be electrically connected to the monitor via cables. Such cables are connected to the medical electrode assemblies via connectors such as snap buttons or alligator clips.

More recent technologies allow for a wearable monitor to be directly connected to medical electrode assemblies, without the use of such cables. An example of a wearable monitor is described in International Patent Application No. PCT/CA2016/050192.

The mechanical stability of the interface between the medical electrode assembly and the patient's skin is key in obtaining a satisfactory signal. For instance, in ambulatory monitoring applications, patients are physically active and the weight of cables and/or the weight of the monitoring equipment can generate forces on the medical electrode assemblies adhered to the patient's skin. Those forces can move the medical electrode assemblies relatively to the patient's skin and consequently introduce noise in the signal due to the variation in the impedance of the interface between the medical electrode assembly and the patient's skin.

Although existing medical electrode assemblies and medical tape were satisfactory to a certain degree, there remains room for improvement.

SUMMARY

For instance, in order to reduce the noise introduced in the signal degradation caused by movements of electrodes, health professionals can apply medical tape which covers the medical electrode assemblies including connecting cables. Such usage of medical tape is burdensome in applications which require disconnecting and reconnecting the electrical connection to the electrode.

In accordance with an aspect, there is provided a wearable monitor comprising a housing having at least two electrode connectors, and a monitoring unit housed within the housing and being connected to the electrode connectors, the monitoring unit having a computer-readable memory having stored thereon electrogram data corresponding to a signal received from medical electrode assemblies adhered to a patient and connected to the electrode connectors over a period of time, the electrogram data having a noise burden of less than ten percent.

In accordance with another aspect, there is provided an extended-adhesive electrode comprising: a medical electrode assembly having an inner face adhered to a patient's skin, and an electrode connector; and an adhesive extender having a unitary flexible sheet with an aperture and an adhesive face, the adhesive face having an inner portion adhered to the medical electrode assembly, and an outer portion adhered to the patient's skin surrounding the medical electrode assembly, with the aperture exposing the electrode connector.

In accordance with another aspect, there is provided a method of applying at least one extended-adhesive electrode to a patient's skin, the method comprising the steps of: mounting at least one medical electrode assembly to the patient's skin, each medical electrode assembly having an electrode unit with a connector facing opposite the patient's skin; and adhering an adhesive extender on each medical electrode assembly and on the patient's skin surrounding the adhered medical electrode assembly, each adhesive extender surrounding the connector.

In accordance with another aspect, there is provided an adhesive extender for use in applying a medical electrode assembly to a patient's skin, the medical electrode assembly having an electrode connector, the adhesive extender comprising: an adhesive extender having a unitary flexible sheet with an aperture and an adhesive face, the aperture being sized to expose the connector, the adhesive face having an inner portion and an outer portion extending away from the inner portion; wherein, during use, the inner portion is adherable to the medical electrode assembly and an outer portion is adherable to the patient's skin surrounding the medical electrode assembly, with the aperture exposing the electrode connector.

In accordance with another aspect, there is provided a kit of parts for use in applying an extended-adhesive electrode to a patient's skin, the kit of parts comprising: a medical electrode assembly having an inner face adherable to a patient's skin, and an electrode connector; and an adhesive extender having a unitary flexible sheet with an aperture and an adhesive face, the aperture being sized to expose the electrode connector, the adhesive face having an inner portion and an outer portion extending away from the inner portion; wherein, during use, the inner face of the medical electrode assembly is adhered to the patient's skin, the inner portion is adhered to the adhered medical electrode assembly and the outer portion is adhered to the patient's skin surrounding the medical electrode assembly, with the aperture exposing the electrode connector.

In accordance with another aspect, there is provided a wearable monitor comprising a housing having at least two electrode connectors, an exposed switch and a monitoring unit housed within the housing and being connected to the electrode connectors and to the exposed switch, the monitoring unit having a clock and a computer-readable memory having stored thereon electrogram data corresponding to a signal received from medical electrode assemblies adhered to a patient and connected to the electrode connectors over a period of time and patient event data indicating one or more moments in time during said period of time at which the exposed switch was triggered. Indeed, when the switch is activated by the patient, the moment of activation by the patient can be implicitly or explicitly indicated in the data file via usage of the clock.

In accordance with another embodiment, there is provided an extended-adhesive electrode comprising: a medical electrode assembly having an inner face adherable to a patient's skin, and an electrode connector exposed on an opposite outer face; and an adhesive extender having a unitary flexible sheet with a first face, a second face being adhesive and opposite the first face, and an aperture, the second face having a greater coverage area than a coverage area of the medical electrode assembly when the medical electrode assembly is adhered to the patient's skin in a manner that, when the adhesive extender is applied to the adhered medical electrode assembly, an inner portion of the flexible sheet material adheres to the medical electrode assembly, an outer portion of the flexible sheet material surrounds the adhered medical electrode assembly and adheres to a surrounding portion of the patient's skin, and the connector of the medical electrode assembly is exposed for connection across the aperture.

Many further features and combinations thereof concerning the present improvements will appear to those skilled in the art following a reading of the instant disclosure.

DESCRIPTION OF THE FIGURES

In the figures,

FIG. 1 is an exploded side view of an example of an extended-adhesive electrode to be adhered to the patient's skin;

FIG. 2 is a cross sectional side view of an example of an extended-adhesive electrode adhered to the patient's skin;

FIG. 3 is a top elevation view of the extended-adhesive electrode of FIG. 2;

FIG. 4 is a front view of a patient wearing a wearable monitor of for obtaining electrocardiogram data; and FIG. 5 is a graph of an example of ECG data obtained using the wearable monitor of FIG. 4;

FIG. 6 is an oblique, exploded view, showing a wearable monitor and medical electrode assemblies of FIG. 4;

FIG. 7 is an oblique, exploded view of the wearable monitor of FIG. 4

FIG. 8 is a plan view of a mould assembly used in the manufacture of the wearable monitor of FIG. 4;

FIG. 9 is an oblique view, showing a portion of an electronic device having two housing members and a joint member;

FIG. 10 is an oblique view showing a half of the mould of FIG. 8;

FIG. 11 is a cross-sectional view, fragmented, taken along lines 11-11 of FIG. 8; and FIG. 12 is a cross-sectional view, fragmented, taken along lines 12-12 of FIG. 8.

DETAILED DESCRIPTION

FIG. 1 shows an exploded side view of an extended-adhesive electrode 10. As shown, the extended-adhesive electrode 10 includes a medical electrode assembly 12 and an adhesive extender 14.

In the illustrated example, the medical electrode assembly 12 has an adhesive collar 16 having an inner face 18 and an opposite outer face 20. The inner face 18 is adhesive and can include an adhesive coating 18a covering a body of porous material, for instance. The adhesive collar 16 has a relatively flat shape in this example. The medical electrode assembly 12 is generally provided with a release liner 21 at the inner face 18 to ease handling of the medical electrode assembly 12 prior to mounting to the patient's skin 22.

FIG. 2 shows the extended-adhesive electrode 10 applied to the patient's skin 22. As depicted, the medical electrode assembly 12 has an internal wall 24 defining a collar opening 26 in which is received an electrode unit 28. In this example, the electrode unit 28 is permanently adhered to the outer face 20 of the adhesive collar 16 using an adhesive sheet 30. As shown, the electrode unit 28 has an electrode connector 32 exposed at the outer face 20 which is electrically connected to a gel 34 exposed at the inner face 18. The gel 34 is electrically conductive as known in the art. In alternate embodiments, the details of the medical electrode assembly's construction can vary.

During use, a signal path is created between the patient's skin 22, the gel 34, the electrode connector 32 and a monitor matingly connected to the electrode connector 32 of the medical electrode assembly 12 via cable 31 and connector 33.

As it will be understood, any other type of medical electrode assembly having an inner face adherable to a patient's skin and an electrode connector can be used. The adhesive extender can be adapted and configured to fit with any type of medical electrode assembly.

The monitor is used to receive a signal via the signal path created when the medical electrode assembly 12 is applied to the patient's skin 22. It can record and/or display electrogram data (e.g., EEG data, ECG data) representing the signal over time. The monitor can be an external monitor connectable to the medical electrode assembly 12 using the cable 31 terminated with the connector 33 matingly connectable to the electrode connector of the medical electrode assembly 12. The connectors can be provided, for instance, in the form of snap button or alligator clips. Any other suitable type of connector or connector assembly can be used. The monitor can be a framed unit located in a room. Alternately, the monitor can be a wearable monitor, such as a Holter monitor or an alternate form of wearable monitor such as will be described below.

The adhesive extender 14 has a unitary flexible sheet 39 with an aperture 44 and an adhesive face 38. The adhesive face 38 has an inner portion 46 adherable to the medical electrode assembly 12, and an outer portion 48 adherable to the patient's skin surrounding the medical electrode assembly 12 (see FIGS. 2 and 3). When the inner portion 46 is adhered to the medical electrode assembly 12 and the outer portion 48 is adhered to the patient's skin surrounding the medical electrode assembly 12, the aperture 44 exposes the electrode connector 32.

Referring back to FIG. 1, the unitary flexible sheet 39 has a first face 40 opposite the adhesive face 38. The adhesive face 38 can include an adhesive coating 38a. The adhesive extender 14 is generally provided with a release liner 41 at the adhesive face 38 to ease handling of the adhesive extender 14 prior to use.

As best seen in FIG. 2, the adhesive extender 14 has an internal perimeter P defining the aperture 44 which is sized to expose the electrode connector 32 of the medical electrode assembly 12. As depicted, in this example, the aperture 44 receives the electrode connector 32 which protrudes from the outer face 20 of the medical electrode assembly 12. In an alternate embodiment, the electrode connector of the medical electrode assembly can be recessed from the outer face and nonetheless be exposed for connection by the aperture when the extended-adhesive electrode is applied on the patient's skin.

As shown, the adhesive face 38 has a greater coverage area 48' than a coverage area 46' of the medical electrode assembly 12 when adhered to the patient's skin in a manner that, when applied to the medical electrode assembly 12, an inner portion 46 of the unitary flexible sheet 39 adheres to the medical electrode assembly 12, an outer portion 48 of the unitary flexible sheet 39 surrounds the adhered medical electrode assembly 12 and adheres to a surrounding portion 50 of the patient's skin 22, and the electrode connector 32 of the medical electrode assembly 12 is exposed for connection across the aperture 44.

In other words, the inner portion 46 surrounds the aperture 44 and has an area substantially corresponding to that of the outer face 20 of the adhesive collar 16 of the medical electrode assembly 12. The outer portion 48 extends away from the inner portion 46. In a case where the adhesive extender has a circular shape, the outer portion radially extends away from the inner portion.

Still referring to FIG. 2, the inner portion 46 of the adhesive extender 14 is adhered to the outer face 20 of the adhesive collar 16 of the medical electrode assembly 12, and the outer portion 48 of the adhesive extender 14 is adhered to surrounding skin 50 of the patient. As it will be understood, the surrounding skin 50 surrounds the patient's skin 22. In this example, the inner portion 46 of the adhesive extender 14 is adhered over the adhesive sheet 30. The unitary flexible sheet can adapt to and cover the shape of the medical electrode assembly 12.

As it will be understood, the adhesive extender 14 can allow to further secure the medical electrode assembly 12 to the patient's skin 22 while allowing connection and disconnection of a cable 31 to the electrode connector 32 of the medical electrode assembly 12 without removing the adhesive extender 14 nor the medical electrode assembly 12. As will be exemplified below, it was found that use of the adhesive extender 14 can promote the integrity of the signal path during use.

FIG. 3 shows a top elevation view of the extended-adhesive electrode 10. In this example, the aperture 44 has a first radius $R_1$ of about 0.6 cm whereas an external diameter D of the outer portion 48 of the adhesive extender has a second radius $R_2$ of about 3.1 cm. The area of this example of the adhesive extender 14 is thus about 29 $cm^2$. These dimensions can vary depending on the application and the type of medical electrode assembly used. For instance, this area can be greater than 25 $cm^2$ and the external diameter D can be of more than 6 cm.

As shown, the shape of the adhesive extender 14 is circular in this example. Any suitable shape of the adhesive extender can be used. It can be satisfactory to use adhesive extender having a shape with rounded vertices in some applications. For instance, the adhesive extender can have a square shape with four rounded vertices, a hexagonal shape with six rounded vertices, and the like. Rounded vertices can lead to better detachment resistance by contrast with sharp vertices.

In this example, the first face 40 of the adhesive extender 14 includes fabric. In an alternate example, the first face includes plastic or any other suitable material.

With reference to the embodiment shown in FIG. 2, a method for applying the extended-adhesive electrode 10 to the patient's skin is described. It is understood that more than one extended-adhesive electrode 10 can be applied to the patient's skin. The method includes a step of mounting the medical electrode assembly 12 to the patient's skin 22, with the electrode connector 32 of the electrode unit 28 facing opposite from the patient's skin 22.

The method includes a step of adhering the adhesive extender 14 on the medical electrode assembly 12 (prior or after the adhesive electrode assembly 12 is mounted to the patient's skin 22) such that the aperture 44 surrounds the electrode connector 32 and also extends away from the medical electrode assembly 12 to provide adherence to the surrounding skin 50 of the patient. The adhesive extender can be positioned concentrically relative to the medical electrode assembly 12.

As it will be understood, the medical electrode assembly 12 can be sold assembled in which case the step of mounting the medical electrode assembly includes adhering the medical electrode assembly 12 to the patient's skin 22. In an alternate example, the medical electrode assembly can be sold separately, and the medical electrode assembly can be mounted on the patient (i.e. the adhesive collar is adhered to the patient's skin, the collar opening is filled with electrically conductive gel, the electrode unit is adhered to an outer face of the adhesive collar with an electrode face electrically connected to the gel and the electrode connector facing away from the gel).

Wearable monitors can be used. Such wearable monitors can be light-weight and portable and have a relatively small footprint. Each wearable monitor can be connected to at least two medical electrode assemblies adhered to two spaced-apart patient's skin portions.

These wearable monitors allow electrogram data to be obtained during few seconds in some applications. In some other applications, it is desirable to obtain the electrogram data during longer periods of time. For instance, during more than four days and even more than seven days. In these applications, the wearable monitor follows the patient in her/his daily activities while the electrogram data are being obtained. Although the existing wearable monitors were satisfactory to a given degree, there remains room for improvement. Especially for these applications where electrogram data are obtained during hours and even during days. Indeed, it was found that the daily activities of the patient could prevent suitable connections between the medical electrode assemblies and the patient's skin, thus impacting negatively the integrity of the signal path and the quality of the signal received by the medical electrode assemblies.

It was found that by using extended-adhesive electrodes instead of the usual medical electrode assembly, the adherence of the medical electrode assemblies relative to the patient's skin could be enhanced and thus positively impact the integrity of the signal path and the quality of the signal receive by the extended-adhesive electrodes.

Referring now to FIG. 4, such a wearable monitor 60 is shown during use. The patient has two extended-adhesive electrodes 10 applied at two of his spaced-apart skin portions 22' and 22", for instance. As shown, the wearable monitor 60 includes a housing 62 having at least two electrode connectors 64 connected to each electrode connector of the two extended-adhesive electrodes 10.

The wearable monitor 60 has a monitoring unit 66 housed within the housing 62 which is connected to the electrode connectors 64 for receiving a signal across corresponding signal paths of the two extended-adhesive electrodes 10.

In this embodiment, the monitoring unit 66 has a computer-readable memory 68 adapted and configured to store thereon electrogram data corresponding to the signal received from the extended-adhesive electrodes 10 applied to the patient and connected to its electrode connectors 64 over a period of time. For instance, the computer-readable memory 68 can include 8 Gb or more of volatile memory which can store electrogram data obtained during over fourteen days. The computer-readable memory can be a non-volatile memory in an alternate embodiment.

In an embodiment, the stored electrogram data are provided in a table having a plurality of difference of potential values corresponding to a sequence of moments in time. A clock system can be used to control the sequence of moments in time and ensure that the intervals remain regular over the entire storing period and are thus predetermined, or to store a second data set of moments in time corresponding to the difference of potential values, for instance. The difference of potential values can be plotted as a function of time to display the electrogram, for instance.

The table can be stored in a numeric file which can be consulted and/or processed using a computer (e.g., .csv file, .xls file, .txt file and the like). It is noted that the file can be encrypted depending on the application.

It is envisaged that the wearable monitor 60 is connectable to a remote computer 74 via the electrode connectors 64 for accessing the stored electrogram data. The remote computer 74 can be provided in the form of a personal computer, an electronic tablet, a smart phone, for instance.

In this embodiment, the housing 62 has an exposed switch 70 connected to the monitoring unit 66. When the exposed switch 70 is triggered, the monitoring unit 66 causes patient event data to be stored on the computer-readable memory 68. The patient event data can indicate one or more moments in time at which the exposed switch was triggered. The patient event data can be useful since it provides an indicator to a health professional who can consult the electrogram data at the moments in time at which the switch 70 was triggered by the patient and analyze the associated felt symptoms.

The patient event data can be provided in the form of a table having binary information alongside each difference of potential values to indicate when the patient (or any other third party) triggered the exposed switch 70, for instance. The patient event data can be recorded as a separate data set in the same or in a different memory, such as a file which stores a list of moments in time when the switch was triggered based on the clock system, for instance. Alternately, the patient event data can form part of the same data set. For example, the binary information "1" can be associated to each difference of potential value obtained when the exposed switch 72 was triggered and the binary information "0" can be associated to all the other difference of potential values.

As shown in FIG. 5, the monitoring unit 66 includes a clock 72 having a given sampling rate which is adapted to obtain a difference of potential value via the electrode connectors 64 at each clock count. With a sampling rate of 250 Hz, for instance, each clock count are timely spaced by 4 ms. Any other suitable sampling rate can be used. The monitoring unit 66 can be configured to correct the clock 72 to maintain a given time reference such as the GMT time. In this embodiment, the clock 72 is configured to maintain GMT time for a period of time lasting at least eighteen months.

In one embodiment, the stored electrogram data are in the form of a table including a single column/row including successive difference of potential values. Each difference of potential value can be associated to a given clock count based on the sampling rate at which the electrogram data were sampled using the clock 72. For instance, if the electrogram data are sampled at a sampling rate of 250 Hz, each successive difference of potential value are timely separated by 4 ms so each difference of potential value can be associated with a corresponding moment in time. The monitor can be configured in a manner to store the time and date at which it is activated. The activation can be based on the initial triggering of a switch, for instance, or by the clipping of electrodes, to name another example. Alternately, the monitor can be pre-activated. In this example, electrogram data obtained during 24 hours can have a table including at least 21.6 million successive difference of potential values.

The patient event data can be provided in the form of a table having a plurality of time values obtained based on the sampling rate of the clock 72. More specifically, the patient event data can include, for each trigger of the exposed switch 70, the number of clock counts that were elapsed since the wearable monitor 60 was activated. For example, if the patient triggers the exposed switch 70 ten days after the wearable monitor 60 was activated, the computer-readable memory stores the number "216 million".

The memory can be integrated within the monitoring unit 66 and, when the period of use of the monitoring unit with the patient has ended, the data can be extracted by wired connection to a computer. Alternately, the monitoring unit 66 can have a transmitter for transmitting the signal obtained from the electrodes to a remote computer 74. The transmission of the electrogram data can be performed wirelessly through a network such as the Internet via a wired connection or a wireless conection (e.g., Wifi, Bluetooth, optical). In an embodiment where such a transmitter is provided, the computer-readable memory can be optional. For instance, the transmitter can be configured to transmit the electrogram data to the remote computer 74 continuously as they are obtained. The transmitted electrogram data can be stored or displayed by the remote computer 74. However, in an embodiment where a computer-readable memory is provided, the transmitter can be optional. For instance, the computer-readable memory can be access via a wired connection to the electrode connectors 64 or the computer-readable memory can be removable (e.g., USB key, SIM card and the like).

By using the wearable monitor 60 with the extended-adhesive electrodes 10, it was found that the electrogram data obtained had a lower burden of noise compared to that obtained using a wearable monitor with the usual medical electrode assemblies (without the adhesive extenders). More specifically, the electrogram data obtained when using the extended-adhesive electrodes have a burden of noise less than ten percent. In an embodiment, the burden of noise is less than nine percent, preferably less than eight percent and most preferably less than seven percent. Indeed, the adhesive extenders are believed to favour a better electrical connection between the electrodes and the patient's skin, and also reduce the likelihood of electrode detachment.

The burden of noise is defined as the period of time including noise in the electrogram data divided by the total period of time during which the electrogram data were obtained. For instance, for given electrogram data including two hours of noise over a total of 24 hours of recordings, the burden of noise is about 8.3% thus less than 10 percent.

To identify the periods of time including noise, an identification algorithm can be used. An example of the identification algorithm was used to analyze electrogram data to obtain the noise burden. The electrogram data were provided in the form of ECG data sampled at 250 Hz over 16 bits. The identification algorithm includes the steps of :

i) applying a band pass filter to keep frequency components between 0.5 Hz and 40 Hz to obtain first filtered ECG data.

ii) identifying QRS complexes present in the first filtered ECG datausing, for instance, an identification algorithm such as the one described in "Tyagi, Shivi, and Mahendra Kumar Patil. "QRS Detection using EMD and First Order Gaussian Differentiator." International Journal of Engineering Research and Technology. Vol. 3. No. 2 (February 2014). ESRSA Publications, 2014."

iii) removing, from the first filtered ECG data, data windows associated with the identified QRS complex surrounding each one of the identified QRS complexes. In each identified QRS complex, a reference is typically identified between the R peak and the S peak, at the moment where the negative slope is the greatest (~90% of the time). In certain occurences where this point is difficult to identify (typically less than 10% of the time), the reference was determined based on the moment of the R peak (or, in some occurences, of the S peak), taking into consideration that the typical period of time between the S peak and the R peak can be sufficiently small (~10-30 ms) to be ignored without a significant effect on the results. Each data windows begins 50 ms prior to the reference and ends 100 ms after the reference. FIG. 5 shows an example of first filtered ECG datawith QRS complexes 80 and corresponding data windows 82 shown in dashed lines. This step yields QRS-free data.

iv) filtering the QRS-free data using a high pass filter at 10 Hz to remove P waves and T waves such as the ones shown in FIG. 5 to obtain a PQRST-free data.

v) obtaining a noise value resulting from the integration of each of a plurality of RR intervals of the PQRST-free data over their time duration. Each RR interval represents the data between two successive R peaks of two successive QRS complexes. For instance, FIG. 5 shows first, second and third RR intervals 84, 86 and 88.

vi) determining, for each of the RR intervals, that the corresponding RR interval includes noise when its noise value exceeds a noise threshold. In this embodiment, the noise threshold is defined as 0.6 times the median value of the difference of amplitude between the R peak and the S peak in the identified QRS complexes. The noise threshold can vary, but it will vary the associated noise burden. In this embodiment, the first and second RR intervals 84 and 86 each have a noise value below the noise threshold thus they are not being identified as including noise. The third RR interval 88 has a noise value over the noise threshold and is considered as including noise.

For instance, once this identification algorithm is carried out, calculating the noise burden consists in calculating the period of time including noise $\Delta T_{Noise}$ by summing the period(s) of time corresponding to each of the RR intervals including noise $\Delta T_{Noise,i}$ and dividing the period of time including noise $\Delta T_{Noise}$ by the total period of time $\Delta T$ (which will typically correspond to the period of time for which the monitoring was prescribed by a physician, such as 24 hours, 48 hours, 72 hours, 7 days, 14 days, etc.) during which the electrogram data were obtained, to obtain the noise burden in the form of a time-related % of the stored data which is considered as noise rather than signal. This can be represented in a mathematical relation given by:

$$\text{Noise burden} = \frac{\Delta T_{Noise}}{\Delta T} = \frac{\sum_{i=1}^{i=max} \Delta T_{Noise,i}}{\Delta T}.$$

Experiment 1

An experiment was carried using a wearable monitor 60 as shown in FIG. 4, and which will now be described in greater detail.

The wearable monitor 60 is designed to be used continuously over several days or more, and is made to have water-resistance. In the case of ECG applications, the housing 62 can also require a significant amount of flexibility. Indeed, in particular situations, such as when the patient is sleeping on the side for instance, rigidity of the wearable monitor 60 can cause stress in the adhesive bond between the electrodes assemblies 10 and the patient's skin, which can cause noise in the signal, or even cause the wearable monitor 60 to disconnect from the electrode assemblies 10, or the electrode assemblies 10 to detach from the patient's skin, which is undesirable. For these reasons, elastomeric materials appear as an interesting choice for the housing 62. Moreover, in such applications, a press-switch system 70 can be used to allow the patient to add a marker in a corresponding temporal location in the data file containing the electrocardiogram data, such as to mark a moment in time when the patient feels a particular symptom, for instance. In this manner, the marker can later be used when accessing the electrocardiogram data to identify temporal locations which require a heightened level of attention, for instance. It will be understood that intuitiveness and ease of use can be particularly important in such applications.

In this example, the wearable monitor 60 can be said to be of the integrated connector-type, that is, of the type of wearable monitor which does not use wires to connect to the electrodes, but rather electrode connectors directly integrated here within an elongated, bandage-like housing having the electronic unit integrated therein. More specifically, the housing has an electrode connector at each end of its length. The housing can thus preferably have a significant amount of flexibility and water-resistance.

FIG. 6 shows the wearable monitor 60 without the patient, with the medical electrode assemblies 10 being disconnected. The wearable monitor 60 is elongated and has electrode connectors 94 at each end, which are designed to mate with corresponding connectors 32 of the medical electrode assemblies 10. The connectors between the medical electrode assemblies 10 and the monitoring unit 60 are push-button type connectors in this case, which can offer both mechanical and electrical connection. Any other suitable connector configuration can be used in alternate embodiments. Moreover, it will be noted that the medical electrode assemblies 10 shown in the figure have an optional adhesive extender covering an 'off the shelf' electrode unit. This configuration is used purely for exemplary purposes and any suitable medical electrode assembly can be used in alternate embodiments. The monitoring unit 66 of the wearable monitor 60 is located within a cavity 98 formed between two superposed housing members 116, 118 which are joined to one another by a joint member 120. A central protuberance 100 on the outer one of the housing members 116 coincides with the location of the monitoring unit 66, and bears a depression 86 which can be used by the user to locate the press-switch unit 128.

FIG. 7 shows the housing members 116, 118 of the wearable monitor 60, and the joint member 120, exploded. The housing members 116, 118 can be seen as they are prior to overmoulding the joint member 120. The joint member 120 is designed to be formed only in its overmoulded state, and is not normally seen in a standalone manner as shown in this figure for illustrative purposes. The electrode connectors 94 in this example are female press-button connectors assembled to annular sheets 102 of elastomeric material and are initially separate from the inner one of the housing members 118. The electrode connectors 94 are connected to the electronic unit 126 by wires 104. The electronic unit 126 receives a battery 106, circuit components 108, and the press-switch unit 128 on an electronic board 126, the electronics board 126 itself being received on the housing member 118. When the components are positioned into the mould 150 for overmoulding of the joint member 120, the electrode connectors 94 can be received in and engaged with corresponding features of the mould 150. In alternate embodiments, the type, quantity and diversity of electronic components can vary.

FIG. 8 shows the mould 150 assembled with the wearable monitor 60 trapped therein after overmoulding. The mould 150 can have a suitable internal construction with inserts and a ramification of channels, such as known in the art.

FIG. 9 shows a portion of an example of the wearable monitor having a monitoring unit 66 housed within a housing 62. The housing 62 has two superposed housing members 116, 118 and a joint member 120 connecting edges, or lips 122, 124, of the housing members 116, 118 to one another along at least a portion of a periphery of the housing members 116, 118. The housing members 116, 118 and the joint member 120 are all made of an elastomeric material, and are thus flexible, compressible, and have elasticity. In this example, the monitoring unit 66 is received on a board 126, itself being received on one of the housing members 118, and is covered by the other one of the housing members 116. The monitoring unit 66 is in a sealed cavity 117 between the housing members 116, 118, the sealed cavity 117 is filled with air.

Concerning the joint member 120, it can be seen in FIG. 9 that the joint member 120 has a flange 132 which extends or projects from the adjacent ends 134, 136 of the superposed lips 122, 124. The flange 132 follows the lips 122, 124 continuously along at least a portion of the periphery, and can be said to 'run' along at least a portion of the ends 134, 136 of the lips 122, 124 in an orientation which can be qualified as 'longitudinal'. The joint member 120 further has a plurality of ribs 138. The ribs 138 are arranged in a plurality of opposed pairs 140 which are interspaced from one another along the periphery. Each pair 140 has two opposed ribs 138, with each rib 138 of the pair 140 i) protruding from the flange 132 on a corresponding, opposite side, ii) extending partially along the corresponding face 142, 144 of the flange, and iii) extending partially along the face 146, 148 of the corresponding lip 122, 124. As will now be explained, the joint member 120, including the flange 132 and ribs 138, can be overmoulded to the lips 122, 124 of the housing members 116, 118 in a manner to join the lips 122, 124 to one another and form a sealed joint therebetween.

Indeed, as shown in FIG. 10, the ribs 138 can be formed by correspondingly shaped and configured voids in the mould 150, which will be referred to herein as rib negatives 152. Accordingly, the rib negatives 152 are regularly interspaced from one another in corresponding mould halves 154, 156, with FIG. 2 showing only one half 154 of the mould. The portions of the mould which are located between the rib negatives will be referred to herein as abutments 158.

FIGS. 11 and 12 each show a cross-section showing the wearable monitor 60 trapped between the two mould halves 154, 156, with the overmoulded joint member 120. FIG. 3 is taken transversally across a pair of abutments 158, whereas FIG. 4 is taken transversally across a pair of rib negatives 152, shown here filled by the flange 132 and corresponding ribs 138 of the joint member 120.

As shown in FIG. 11, the pair of abutments 158 from corresponding halves 154, 156 of the mould 150 can be designed to compress the area of the superposed lips which is located between rib negatives during the step of overmoulding the joint member 120. The flange 132 can be seen extending transversally from the ends 134, 136 of the lips 122, 124.

FIG. 12 shows a cross-section taken along a pair of opposed rib negatives 152. As shown in FIG. 4, a portion 160 of the lips located in the rib negatives 152 is free from the compression of the mould 150 prior to feeding the elastomeric material of the joint member 120 into the mould 150. By comparing FIGS. 3 and 4, one can appreciate how the free portions 160 of the lips 122, 124 extend longitudinally between two adjacent abutments 152, and also transversally protrude from an inner portion 162 of the lips 122, 124 which is 'nipped' in compression between two features of the mould 150 which will be referred to herein as nips 164, 166. When the elastomeric material of the joint member 120 is fed in its liquid/viscous state, which can be done along a parallel channel 168 in this example, the surface tension of the elastomeric material under the clamping force of the mould as well as the injection pressure forces and stretches the free portions 160 of the lips 122, 124 apart from one another, but the freedom of movement of the free portions 160 of the lips 122, 124 is limited as adjacent portions of the lips 122, 124 are trapped in compression between the adjacent pairs of abutments 158 and between nips 164. Accordingly, tension is built into the free portions 160 of the lips 122, 124 due to the stretching, and this tension can eventually compensate for the penetrating pressure of the liquid/viscous elastomeric material. A satisfactory amount of the liquid/viscous elastomeric material can be allowed to form the pair of ribs 138 which covers the two opposite faces 146, 148 of the free portion 160 of the lips 122, 124 and, once solidified, join and seal the free portions 160 of the lips 122, 124 to one another. In practice, the channel 168 is also filled with elastomeric material after moulding and forms a trim which is removed after overmoulding. In FIGS. 11 and 12, the trim is not shown for simplicity.

Referring back to FIG. 9, as the longitudinal spacing distance 170 between adjacent ribs 138 is limited, the degree of joining and sealing can be satisfactory even though the opposite faces 146, 148 of the lips 122, 124 are not covered by the joint member 120 between the ribs 138. Indeed, as shown in FIG. 3, between the ribs 138, at the location of the abutments 158, only the adjacent ends 134, 136 of the lips 122, 124 are covered by the flange 132 of the joint member 120 and the faces 146, 148 of the lips 122, 124 are uncovered. Moreover, the interspaced spacings between the ribs 38 along the joint member 120 can act as hinges and allow a greater amount of bending ability/transversal flexibility than if a pair of continuous rib elements extended continuously the periphery of the superposed lips.

Accordingly, the method of joining the lips can include : positioning the lips 122, 124 in a superposed manner in a mould 150 (e.g. such as shown in FIGS. 11 and 12); compressing the superposed lips 122, 124 in a plurality of compression locations (one of which is shown in FIG. 11) with corresponding pairs of abutments 158 of the mould which are interspaced from one another along the length of the lips 122, 124, the plurality of pairs of abutments 158 being interspaced from one another by corresponding pairs of rib negatives 152 (one of which is shown in FIG. 12); and overmoulding the joint member 120 onto the superposed lips 122, 124 in the mould, the joint member 120 having a flange 132 projecting from ends 134, 136 of the lips 122, 124, and a plurality of pairs of ribs 138 filling the rib negatives 152, each rib 138 of a corresponding pair protruding from the flange 132 and extending over a face 146, 148 of a corresponding one of the lips 122, 124.

In this specific embodiment, the thermoformable elastomer (TPE) used was product number CL-40 manufactured under the trademark POLYONE by Versaflex. As shown in FIG. 11, in this embodiment, a sloping portion 169 of the abutments 158 connects the nips 164, 166, and the nips 164, 166 compress the lips 122, 124 by more than 50% of their initial thickness, preferably down to 25-35% of their initial thickness, in this embodiment. Tis configuration can lead to a satisfactory embodiment for at least the illustrated application.

The medical electrode assemblies used were as shown in FIG. 2 and described above. The noise burden was evaluated in the context of a 212 patient clinical study conducted at the Institut Universitaire de Cardiologie et de Pneumologie de Québec (IUCPQ). The identification algorithm and the mathematical relation presented above were used.

Each patient was monitored with a wearable monitor applied for a period of time of 24 hours of continuous ECG recording. Electrogram data were obtained using the wearable monitor for each patient.

Each patient had two spaced-apart medical electrode assemblies mounted to their skin. Some of the patients had no adhesive extender adhered over their medical electrode assemblies, some of the patients had adhesive extenders with a square shape adhered over their medical electrode assemblies and some of the patients had adhesive extenders with a circular shape adhered over their medical electrode assemblies.

For each of the data sets obtained, the noise burden was determined using the algorithm presented above. Table 1 shows, at least in this experiment, that the obtained electrogram data had a reduced noise burden when using square adhesive extenders relative compared with when no adhesive extender is used. Moreover, Table 1 shows, at least in this experiment, a 50% reduction in the noise burden when using circular adhesive extenders relative compared with when no adhesive extender is used.

TABLE 1

Noise burden for different configurations of the wearable monitor

| Configuration of the wearable monitor | Number of patients | Noise burden (%) |
|---|---|---|
| without adhesive extenders | 12 | 13 |
| using two adhesive extenders having a square shape | 19 | 11 |
| using two adhesive extenders having a circular shape | 168 | 6 |

Experiment 2

Another experiment was conducted based on the same context as presented above in Experiment 1, but where the total time period was of 7 days. The skin was prepared by a dry shaving of the skin and cleaning with isopropylic alcohol, and the region of the skin receiving the gel was lightly abraded to remove dead skin, prior to applying the electrode assemblies and adhesive extenders.

TABLE 2

Noise burden 7 day trial of the wearable monitor

| Configuration of the wearable monitor | Number of patients | Noise burden (%) |
|---|---|---|
| using two adhesive extenders having a circular shape | 49 | 12 |

Based on the results presented above, it is predicted that a noise burden of below 22%, preferably below 18%, and more preferably below 15% will be achievable on prescribed time periods of 7 days, preferably 10 days or more, more preferably preferably at least 14 days, using a configuration such as used in experiment 2, and by changing the electrode assemblies during the time period if required due to events such as electrode assembly detachment or the like, on a representative sample of at least 40 patients/occurences, preferably of at least 25 patients/occurences, leading to at least 40, preferably at least 25 collected wearable monitors having data embedded therein having the identified noise burden characteristics and total time period. On samples having lesser total time periods, such as 24 h, 48 h, or 72 hours for instance, the achievable noise burden is predicted to be even lower, such as less than 12, preferably less than 10, more preferably less than 8, based on the experimental results obtained as of the time of filing this application. Moreover, it is believed that the performance obtained in the experiments will remain achievable on larger scales.

The examples described above and illustrated are intended to be exemplary only. The scope is indicated by the appended claims.

What is claimed is:

1. A method using an adhesive extender to apply a medical electrode assembly to a patient's skin, the method comprising the steps of:
   mounting the medical electrode assembly to the patient's skin, the medical electrode assembly having an inner face and an outer face, a connector protruding from the outer face, said mounting the medical electrode assembly to the patient's skin including adhering the inner face to the patient's skin and exposing the connector opposite the patient's skin; and
   adhering the adhesive extender, the adhesive extender having a unitary flexible sheet with an aperture and an adhesive face, the adhesive face having an inner portion surrounding the aperture, and an outer portion surrounding the inner portion, said adhering including adhering the inner portion of the adhesive face onto the adhered medical electrode assembly and adhering the outer portion of the adhesive face to the patient's skin surrounding the adhered medical electrode assembly, the adhered adhesive extender surrounding the connector and exposing the electrode connector through the aperture.

2. The method of claim 1 wherein said adhering the adhesive extender includes positioning the adhesive extender concentrically relative to the medical electrode assembly.

3. The method of claim 1 wherein the medical electrode assembly is a first medical electrode assembly and the adhesive extender is a first adhesive extender further including:
   repeating said steps of mounting and adhering with a second medical electrode assembly and a second adhesive extender, respectively;
   connecting a wearable monitor to the medical electrode assemblies, the wearable monitor having a housing having at least two electrode connectors, and a monitoring unit housed within the housing and being connected to the electrode connectors; and
   using the connected wearable monitor, obtaining electrogram data from a signal received from the medical electrode assemblies over a period of time.

4. The method of claim 3 wherein the period of time corresponds to a portion of a prescribed period of time being of at least 7 days, further comprising:
   disconnecting the wearable monitor from the medical electrode assemblies, detaching the medical electrode assemblies from the patient's skin and replacing the medical electrode assemblies with corresponding replacement medical electrode assemblies adhered to the patient's skin using corresponding replacement adhesive extenders, connecting the wearable monitor to the replacement medical electrode assemblies, and using the wearable monitor, obtaining electrogram data from a signal received from the replacement medical electrode assemblies over a remaining portion of the prescribed period of time.

5. The method of claim 3 wherein the period of time is of at least 8 days and the electrogram data has a noise burden of less than 20%.

6. The method of claim 5 wherein the noise burden is less than 12%.

7. The method of claim 3 wherein the monitoring unit has a computer-readable memory, said obtaining including storing the electrogram data onto the computer-readable memory of the wearable monitor.

8. The method of claim 7 wherein the stored electrogram data are in the form of a table having a plurality of difference of potential values corresponding to a sequence of moments in time, wherein the period of time is more than four days.

9. The method of claim 3 wherein the monitoring unit has a transmitter, said obtaining including transmitting the electrogram data to an external computer.

10. A plurality of wearable monitors including at least 5 wearable monitors each comprising a housing having at least two integrated electrode connectors, and a monitoring unit housed within the housing and being connected to the electrode connectors, the monitoring unit having a computer-readable memory having stored electrogram data corresponding to a signal received, over a period of time, from medical electrode assemblies adhered to a patient and connected to the electrode connectors, the period of time being of at least 48 hours, the stored electrogram data having a noise burden defined as the duration of electrogram data containing noise divided by the period of time, the average noise burden of the plurality of wearable monitors being of less than 22%.

11. The plurality of wearable monitors of claim 10 wherein the average noise burden is of less than 15%.

12. The plurality of wearable monitors of claim 10 wherein the period of time of recorded electrogram data is of at least 6 days.

13. The plurality of wearable monitors of claim 12 wherein the average noise burden is of less than 15%.

14. The plurality of wearable monitors of claim 12 including at least 40 of the wearable monitors.

15. The wearable monitor of claim 10 wherein the electrogram data are in the form of a table having a plurality of difference of potential values corresponding to a sequence of moments in time.

16. The wearable monitor of claim 10 wherein the housing is elongated in shape, has one of the at least two electrode connectors at each one of two longitudinally opposite ends thereof.

17. The method of claim 3 wherein the period of time is of at least 4 days and the electrogram data has a noise burden of less than 20%.

18. The method of claim 3 wherein the period of time is of at least 8 days and the electrogram data has a noise burden of less than 15%.

19. The method of claim 3 wherein the period of time is of at least 4 days and the electrogram data has a noise burden of less than 15%.

20. The method of claim 5 wherein the noise burden is less than 10%.

21. The method of claim 7 wherein the stored electrogram data are in the form of a table having a plurality of difference of potential values corresponding to a sequence of moments in time, wherein the period of time is more than seven days.

22. A system comprising the plurality of wearable monitors of claim 10 and at least two extended-adhesive electrode for each one of the at least 25 wearable monitors, each extended-adhesive electrode comprising a medical electrode assembly and an adhesive extender; the medical electrode assembly having an inner face adherable to a patient's skin, and an electrode connector, the adhesive extender having a unitary flexible sheet with an aperture and an adhesive face, the adhesive face having an inner portion adhered to the medical electrode assembly, and an outer portion adherable to the patient's skin surrounding the medical electrode assembly, with the aperture exposing the electrode connector.

23. The method of claim 1 wherein the unitary flexible sheet is circular around a central axis, the aperture is also circular and disposed concentrically to the unitary flexible sheet, the outer portion being radially external to the inner portion.

24. The method of claim 1, wherein the step of mounting the medical electrode assembly includes removing a first release liner from the inner face before adhering the inner face to the patient's skin, and the step of mounting the adhesive extender includes removing a second release liner from the adhesive face of the adhesive extender before adhering the adhesive face to the outer face of the medical electrode assembly and to the patient's skin.

25. The plurality of wearable monitors of claim 10 wherein said electrogram data containing noise is defined as a sum of periods of time resulting from application of an identification algorithm including the steps of:
   i) applying a band pass filter to keep frequency components between 0.5 Hz and 40 Hz and obtain first filtered ECG data;
   ii) identifying QRS complexes present in the first filtered ECG data;
   iii) removing, from the first filtered ECG data, data windows associated with the identified QRS complex surrounding each one of the identified QRS complexes; and identifying, in each QRS complex a reference between the R peak and the S peak, said data windows beginning 50 ms prior to the reference and ending 100 ms after the reference, yielding QRS-free data;
   iv) filtering the QRS-free data using a high pass filter at 10 Hz to remove P waves and T waves, yielding PQRST-free data;
   v) obtaining a noise value resulting from the integration of each of a plurality of RR intervals of the PQRST-free data over their time duration, wherein each RR interval represents the data between two successive R peaks of two successive QRS complexes;
   vi) determining, for each of the RR intervals, that the corresponding RR interval includes noise when its noise value exceeds a noise threshold defined as 0.6 times the median value of the difference of amplitude between the R peak and the S peak in the identified QRS complexes.

26. The plurality of wearable monitors of claim 10 wherein the noise is within the 0.5 Hz to 40 Hz range.

27. The plurality of wearable monitors of claim 25 wherein the noise is above 10 Hz.

28. the plurality of wearable monitors of claim 10 wherein the noise has an amplitude above 0.6 times a median value of differences of amplitudes between the R peaks and the S peaks in the electrogram data.

* * * * *